(12) United States Patent
Edwards et al.

(10) Patent No.: US 10,362,204 B2
(45) Date of Patent: Jul. 23, 2019

(54) ILLUMINATED OBJECT VIEWING AND RETRIEVING TOOL

(71) Applicant: GENERAL TOOLS & INSTRUMENTS, Secaucus, NJ (US)

(72) Inventors: Christopher Edwards, Wappingers Falls, NY (US); Adam L. Boggia, New York, NY (US)

(*) Notice: Subject to any disclaimer, the term of this patent is extended or adjusted under 35 U.S.C. 154(b) by 21 days.

(21) Appl. No.: 15/359,980

(22) Filed: Nov. 23, 2016

(65) Prior Publication Data

US 2017/0150020 A1 May 25, 2017

Related U.S. Application Data

(60) Provisional application No. 62/260,105, filed on Nov. 25, 2015.

(51) Int. Cl.
| | |
|---|---|
| H04N 5/225 | (2006.01) |
| B25J 1/02 | (2006.01) |
| A61B 1/00 | (2006.01) |
| A61B 34/30 | (2016.01) |

(52) U.S. Cl.
CPC .............. *H04N 5/2256* (2013.01); *B25J 1/02* (2013.01); *A61B 1/00* (2013.01); *A61B 34/30* (2016.02); *H04N 2005/2255* (2013.01)

(58) Field of Classification Search
CPC .......... H04N 5/2256; A61B 1/00; A61B 34/30
See application file for complete search history.

(56) References Cited

U.S. PATENT DOCUMENTS

| | | | | |
|---|---|---|---|---|
| 6,419,626 B1* | 7/2002 | Yoon | ................. | A61B 1/00052 600/103 |
| 2007/0151391 A1* | 7/2007 | Larkin | ................... | A61B 34/70 74/490.06 |
| 2010/0250000 A1* | 9/2010 | Blumenkranz | ........ | A61B 34/30 700/258 |
| 2013/0306112 A1* | 11/2013 | Blumenkranz | ........ | A61B 34/30 134/34 |

(Continued)

OTHER PUBLICATIONS

An Open-Source 3D Printed Underactuated robotic gripper; Tlegenov; 2014.*

(Continued)

*Primary Examiner* — Luis Perez-Fuentes

(57) ABSTRACT

An illuminated object viewing and retrieval tool having a body including a control rod guide portion and a housing, a display screen mounted on the housing, an elongated flexible member extending from the control rod guide portion and a control rod extending through an open passage of the control rod guide portion to an outer end connected to a grasping mechanism having finger elements that are movable relative to an outer housing mounted to the control rod guide portion and which expand outwardly relative to one another and the open end of the outer housing, a camera device including a lens mounted within the outer housing to record images through the outer open end of the outer housing and a light source mounted within the outer housing adjacent the lens to cast light outwardly of the outer open end of the outer housing, and power source for connecting to the camera device, the light source and the display screen so that images from the camera lens may be viewed on the display screen.

18 Claims, 12 Drawing Sheets

(56) References Cited

U.S. PATENT DOCUMENTS

| | | | | |
|---|---|---|---|---|
| 2014/0213848 | A1* | 7/2014 | Moskowitz | A61B 1/00133 600/106 |
| 2014/0275772 | A1* | 9/2014 | Chuda | A61M 16/0418 600/104 |
| 2016/0367119 | A1* | 12/2016 | Ouyang | A61B 1/00034 |
| 2017/0188793 | A1* | 7/2017 | Ouyang | A61B 1/00016 |
| 2017/0281298 | A1* | 10/2017 | Blumenkranz | A61B 34/30 |
| 2018/0132700 | A1* | 5/2018 | Ouyang | A61B 1/00039 |
| 2018/0256009 | A1* | 9/2018 | Ouyang | A61B 1/00048 |

OTHER PUBLICATIONS

Two-Phased Controller for a Pair of 2-DOF Soft Fingertips based on the qualitative relationship between joint angles and object location; Yamakaki; 2010.*

An Open-Source 3D Printed Underactuated robotic gripper; Tlegenov; 2014. (Year: 2014).*

Two-Phased Controller fora Pair of 2-DOF Soft Fingertips based on relationship between joint angles; 2010 (Year: 2010).*

Google search for NPL (Year: 2019).*

* cited by examiner

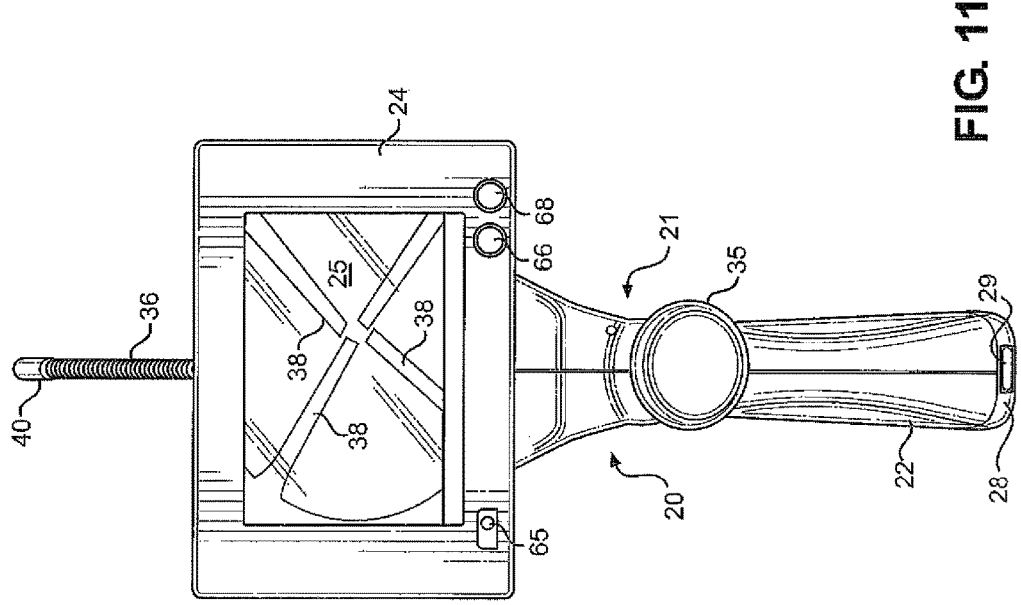

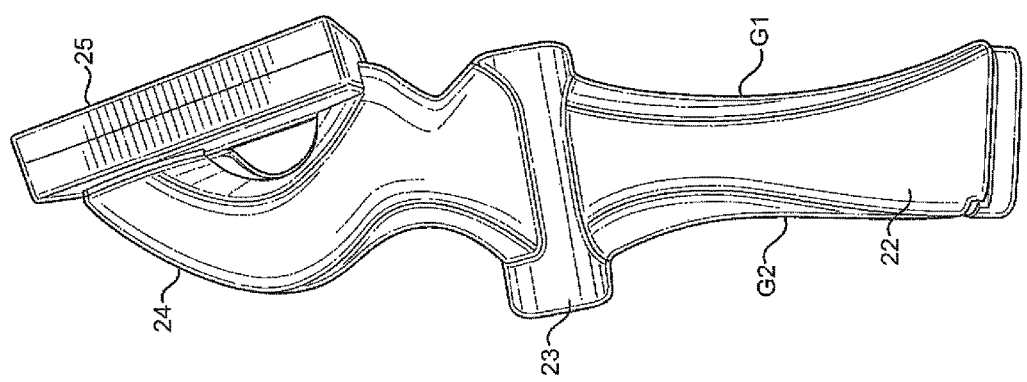

ILLUMINATED OBJECT VIEWING AND RETRIEVING TOOL

BACKGROUND OF THE INVENTION

Field of the Invention

The present invention is general directed to the field of tools used to a combination tool for grasp objects that are in locations or areas that are difficult, or not possible, to grasp and retrieve by hand, such as parts or components of objects that fall or are accidental dropped or become loose in hard to reach areas such as behind, within or under machinery or beyond locked or closed doors or panels in places that can only be accessed by elongated and narrow retrieving tools or devices. More particularly, the invention is directed to a combination retrieving tool having an elongated and generally flexible tubular member for supporting a control rod. The control rod is connected to an outer grasping claw including a plurality of deployable and movable fingers that are operably controlled by the rod to engage about an object to be retrieved. An end or tip portion or housing of the tool is secured to the flexible tubular member and houses a camera device including a lens and illuminating LEDs for use to illuminate areas to be scanned by the lens. The camera and illuminating LEDs facilitate the manipulation of the grasping claw when retrieving of objects. Further, the combination tool includes a display screen mounted to an operating handle of the tool which displays images captured by the camera lens thereby aiding a user in manipulating the tool relative to an object to be retrieved during use.

Brief Description of the Related Art

Retrieving tools having elongated and somewhat flexible rods from which mechanical grasping fingers or claws may be extended and expanded to surround and subsequently engage or grasp a remotely located object are known in the art. Likewise, borescopes are known which include a camera lens to be carried at a tip of an elongated rod so that images captured by the camera lens may be electronically communicated to a remote viewing screen so that images may be viewed by an operator of the scope. There is a need in industry to provide for a tool or tool combination which increase the utility and effectiveness of the currently existing retrieving tools and borescopes.

SUMMARY OF THE INVENTION

The present invention is directed to a combination retrieving tool and remote viewing scope including a body having an operating handle and a viewing screen mounted thereto which is powered by way of a plurality of batteries mounted within the handle and wherein a flexible hollow tubular member extends from the handle to a forward tip portion on which an outer housing is secured. Mounted within the outer housing is a camera device including a lens which is electronically connected to the viewing screen so that images captured by the camera lens are readily viewable by an individual using the tool. Mounted at the tip of the outer housing and surrounding the camera lens are a plurality of LEDs that are used to illuminate an area at which the camera lens is directed. An amount of power to the LESs may be increased or decreased to regulate an amount of light that is broadcast from the LEDs by use of a pair of switch buttons mounted in a housing in which the viewing screen is mounted. By depressing one of the switches, power is increased to the LEDs to thereby increase the illumination of the LEDs and by depressing the other of the switches, power to the LEDs is reduced to thereby decrease the amount of light being broadcast from the LEDs. Power to the switch buttons and the viewing screen is controlled by an ON/OFF switch Mounted to the body of the tool.

Mounted in surrounding relationship of the camera lens at the tip of the tool rod and between the LEDs are a plurality of gripping fingers which may be formed of a flexible or spring like material so that the fingers may by operable to flexibly or resiliently engaged and grasp and object that is being viewed on the viewing screen of the tool. The deployment of the grasping fingers is controlled by a control rod mounted within the hollow tubular member and to which the fingers are mounted. The control rod has an inner end that extends through the body of the tool below the viewing screen and terminates at a knob that can be grasped by a user. In a non-deployed position, the grasping fingers are drawn into close orientation with respect to one another either in close proximity to an open end of the outer housing of the tool or slightly within the open end of the outer housing. By urging the knob toward the handle, the control rod is forced from the open end of the outer housing of the tool so as to be forward of the camera lens. The control rod is connected to the grasping fingers such that as the control rod is forced in a direction of the open end of the outer housing of the tool, the grasping fingers are deployed outward relative to the outer housing. Due the spring-like structure of the fingers, the fingers will automatically open outwardly relative to one another as the control rod moves in the direction of the outer housing of the tool. When deployed, the grasping fingers may be place about an object to be grasped and retrieved, after which, the operator may release the knob, thereby allowing a spring mechanism within the body and which is engaged with the control rod, to automatically force or urge the control rod toward the handle of the tool and thus causing the grasping fingers to be drawn toward one another and at partially into the outer housing thereby securely grasping the object to be retrieved. After being grasped, the tool with the hollow tubular rod is pulled from the area in which the object was positioned until being positioned to be easily handled by the individual using the tool.

In the embodiment shown in the drawings, the tips of the fingers are curved or bent inwardly toward one another to facilitate grasping an object and to prevent an object that has been grasped from sliding free of the fingers between the ends of the fingers.

BRIEF DESCRIPTION OF THE DRAWINGS

A better understanding of the invention will be had with reference to the accompanying drawings wherein:

FIG. 11 is an illustrational view showing an image displayed on the tool viewing screen including the position of the grasping fingers; and FIG. 12 is a front perspective view of the body of the tool of the invention showing the viewing screen and grips for the handle.

DESCRIPTION OF THE PREFERRED EMBODIMENT

Figure 4:
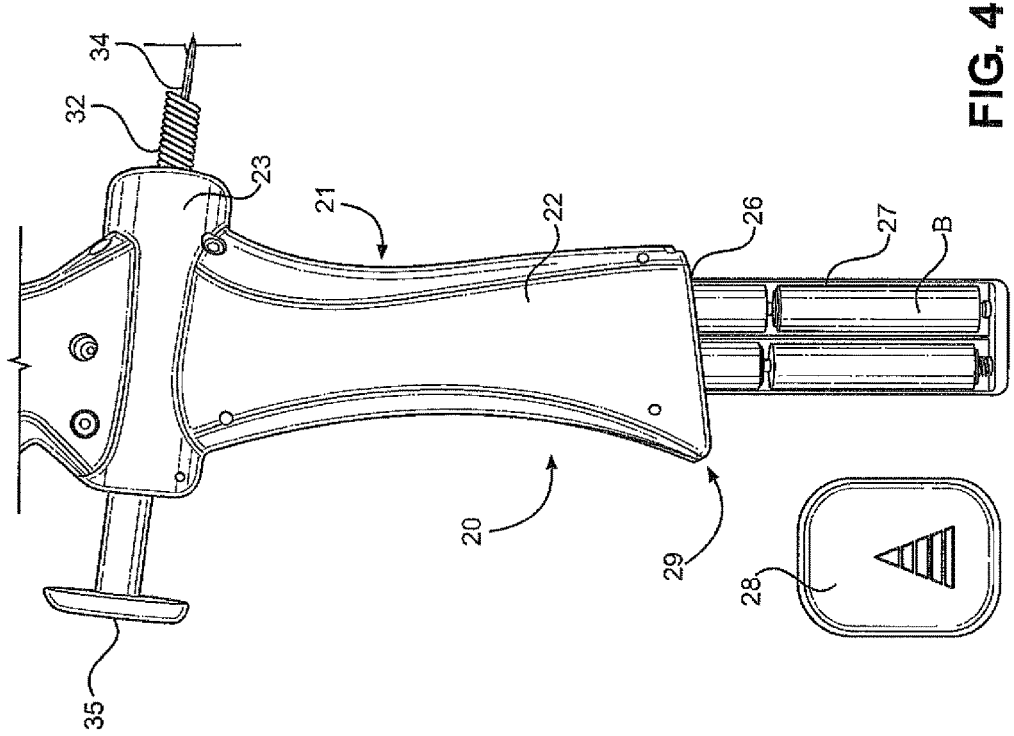
FIG. 4 is a side view of the handle of the tool of the invention showing a battery cover removed from the bottom of the handle and a removable battery tray partially removed from a housing defined within the handle and having portions broken away to show an inner steel control rod that is connected to a control knob of the tool.

With continued reference to the drawings, the illuminated object viewing and retrieval tool 20 of the invention includes a body 21 including a handle 22, a central control rod guide portion 23 above the handle and an upper housing 24 in which a viewing screen 25 is mounted. The handle is generally hollow and defines an inner battery housing 26 in which a battery support tray 27 is removably mounted. With reference to FIG. 4, in the embodiment shown, four AAA batteries "B" are used to provide power to components of the tool and are mounted on the support tray after a battery cover 28 is removed from a bottom 29 of the handle. The body 21 is preferably molded from ABS plastic material. To provide good user gripping engagement with the handle of the tool, the handle may also include overmolded softer plastic grips G1 and G2 along a front and rear of the handle 22 as shown in FIG. 12.

Figure 3:
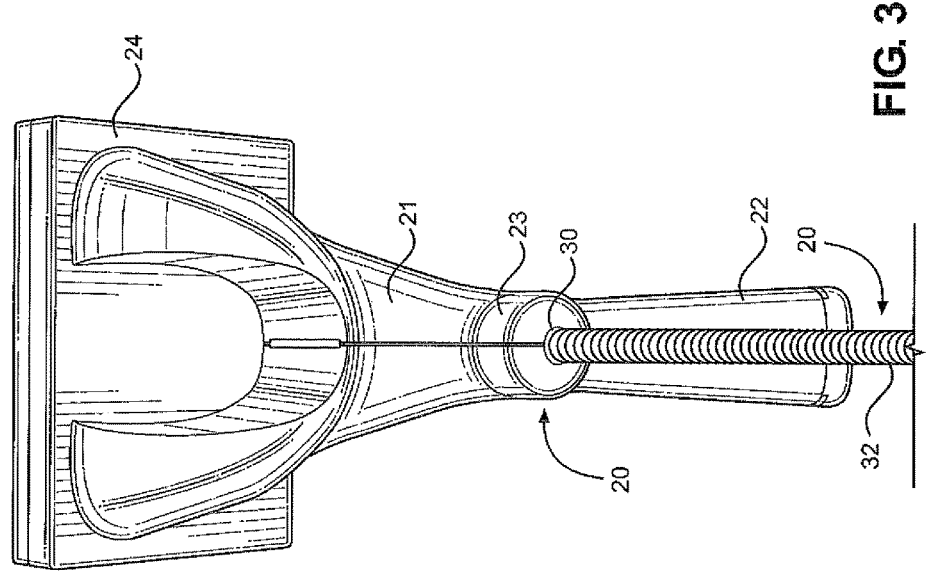
FIG. 3 is a rear view of the body including the handle and viewing screen housing of the invention.
Figure 10:
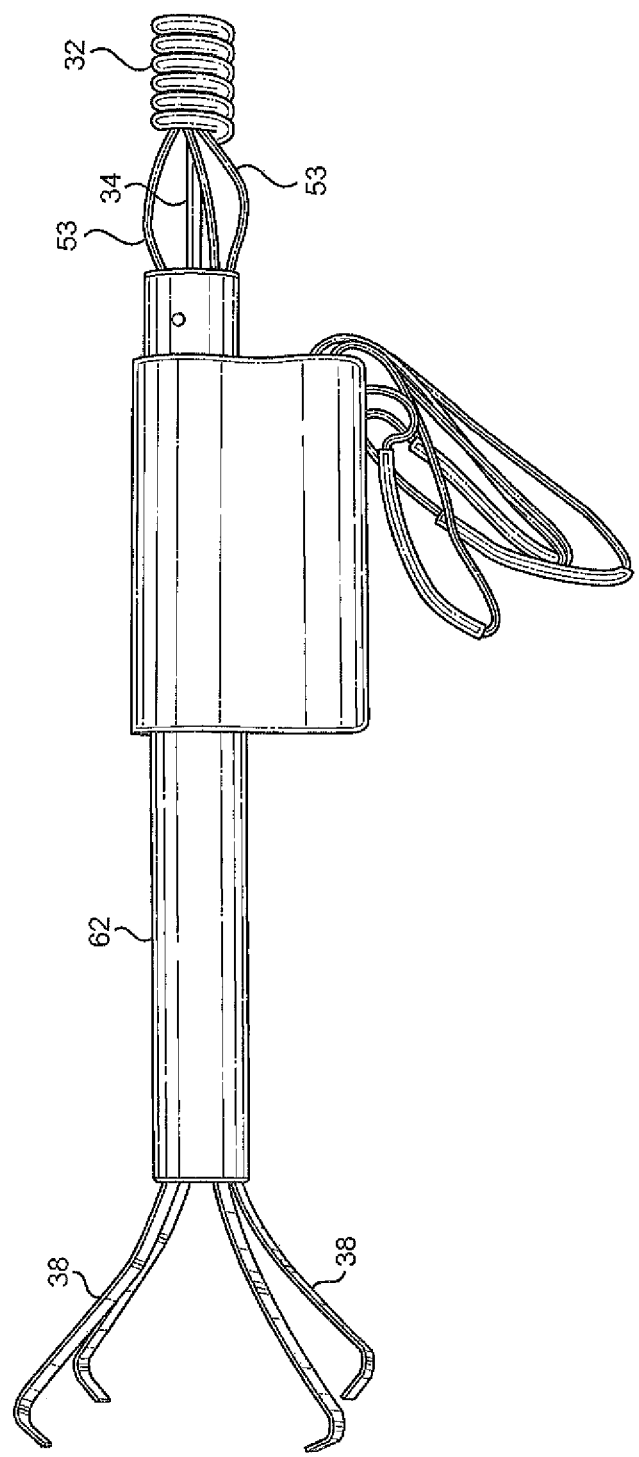
FIG. 10 is a side view of an inner hollow rod with the outer housing sections shown in FIGS. 6-9 removed to show the control rod that extends through the tool body and to the grasping fingers for controlling the opening and closing of the grasping fingers.

The central control rod guide portion 23 of the body 21 defines an open passage 30 in which an inner portion of an elongated flexible tubular member 32 of the tool is secured and through which an inner steel control rod 34 extends, see FIGS. 3, 4 and 10. The tubular member 32 may be formed as a tightly wound spring that may extend up to several feet from the body 21 to an outer end portion 36 to which a two piece outer housing 40 is secured. An inner end of the control rod is mounted to a knob 35 which is used by a person to push the control toward the end portion 36 of the tubular member 32. The tubular member may also be constructed of a steel material, such as a brushed steel.

Figure 1:
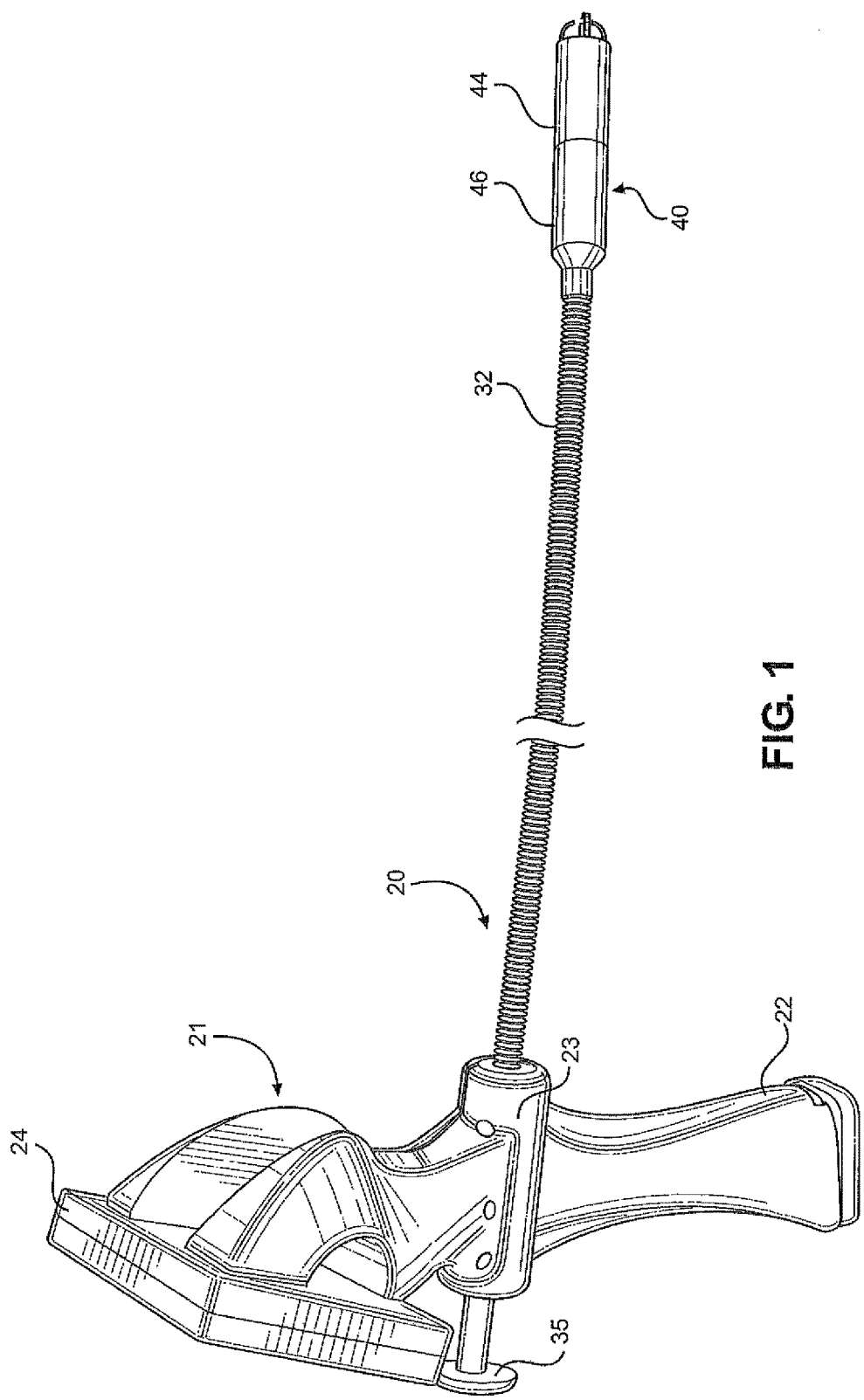
FIG. 1 is a side perspective view of the illuminated object viewing and retrieval tool of the invention showing a tool body including grip or handle and having a viewing screen mounted thereto and from which extends a flexible tubular member through which a control rod extends for adjustably manipulating a grasping mechanism and also wherein a camera device is mounted within an outer housing connected at an end of the tubular member with LEDs being mounted surrounding a camera lens within the outer housing.
Figure 5:
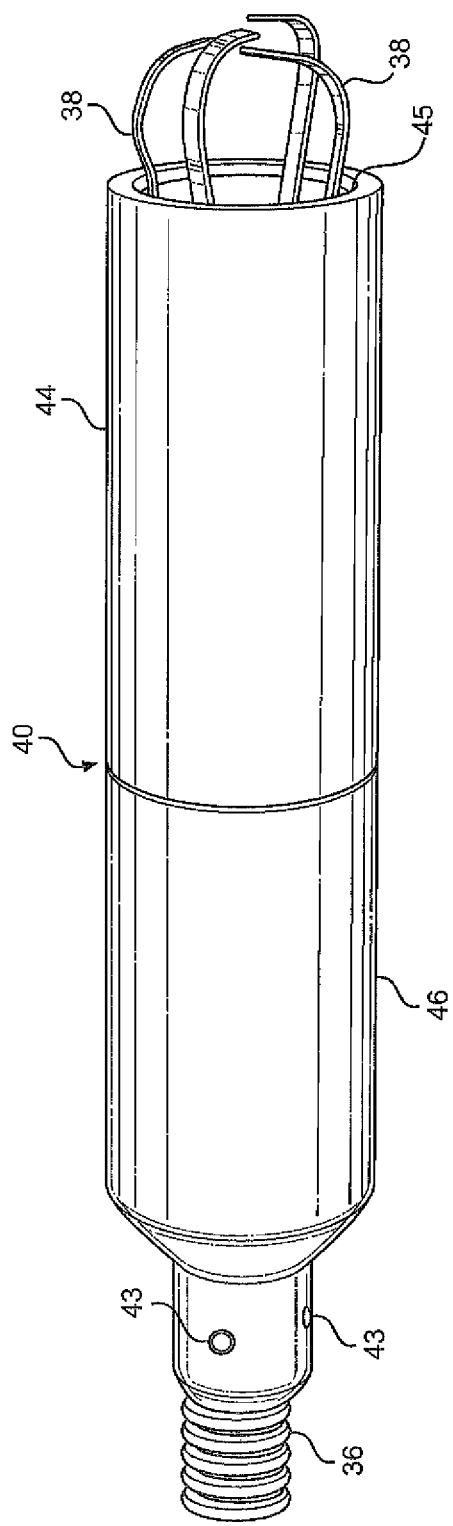
FIG. 5 is an enlarged view of a camera lens and grasping mechanism mounted within an outer housing secured to an end portion of the flexible tubular member and wherein fingers of the grasping mechanism are in a first non-deployed position.
Figure 6:
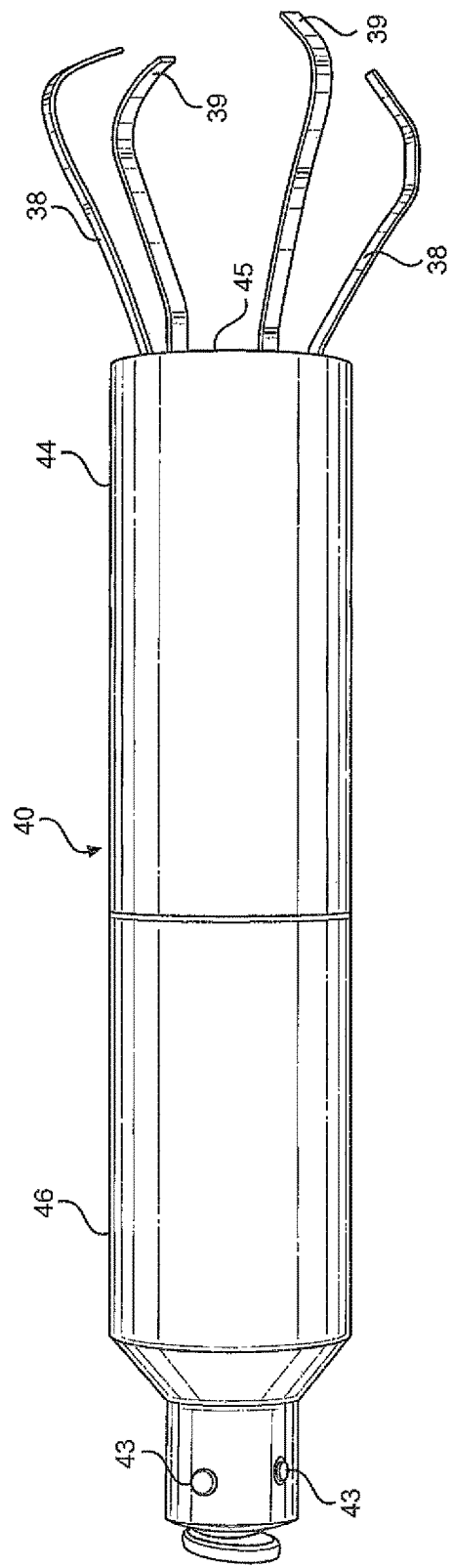
FIG. 6 is a side view of the camera lens, and grasping mechanism and outer housing of FIG. 5 showing the grasping fingers in a outwardly extending deployed position.
Figure 7:
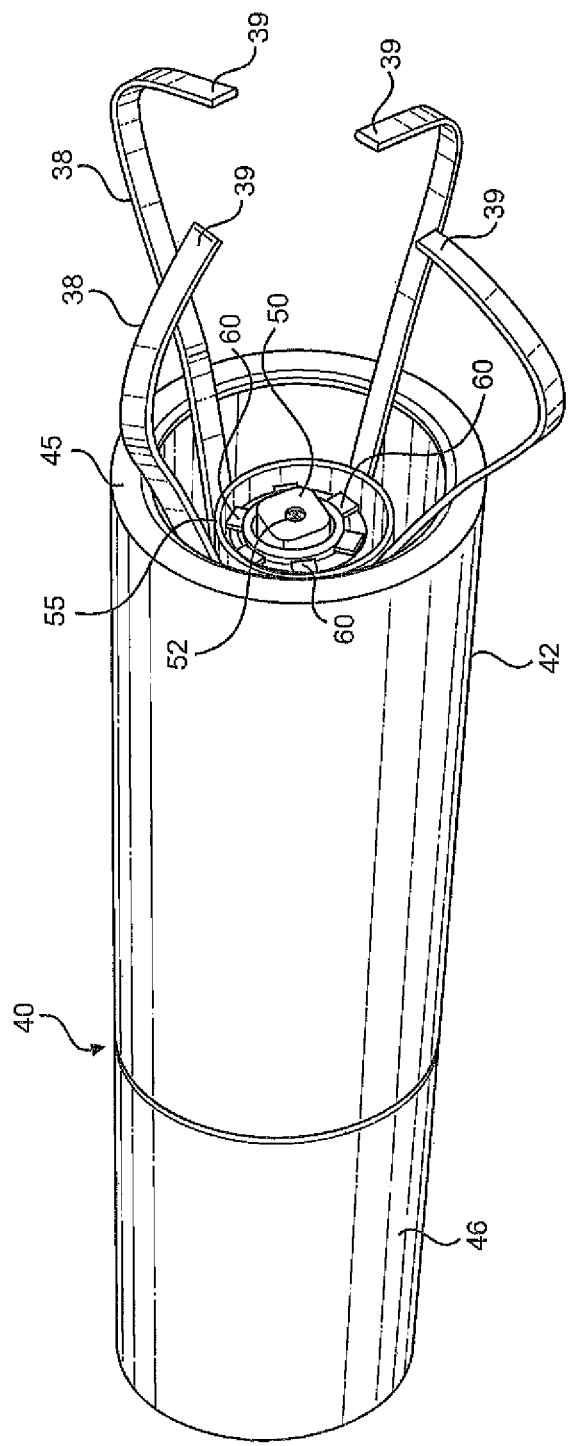
FIG. 7 is a perspective end view of an open end of the camera lens and grasping mechanism containing outer housing of FIG. 6 showing the camera lens centered relative to illuminating LEDs.

The operating knob 35 is used to apply force to urge the control rod to deploy grasping fingers 38 of a grasping mechanism 42 which is normally at least partially positioned within an outermost tubular portion 44 of the two piece housing 40. With reference to FIGS. 1 and 5, when the knob 35 is in a first position spaced from the body 21, as shown in FIG. 1, curved end portions 39 of the grasping fingers remain non-deployed and closely spaced adjacent an outlet opening 45 of the outermost tubular portion 44 of the two piece housing 40. An innermost tubular portion 46 of the two piece housing 40 is mounted to the outer end portion of the flexible tubular member 32 such as by using pins or set screws 43 as shown in FIG. 5. When a user pushes on the knob to urge it toward the body 21, an outer end of the control rod connected to the grasping fingers 38 forces the fingers outwardly of the outlet opening 45 as shown in FIGS. 6 and 7. The grasping fingers are spring biased relative to one another so that they are automatically opened relative to one another to a deployed position thereof when urged outwardly of the outlet opening 45. In the deployed position, the fingers may be positioned about an object to be retrieved such that, as the control rod is activated to draw the grasping fingers back toward the outlet opening 45, the fingers 38 will grasp the object as the fingers are drawn or urged into the closed position thereof as shown in FIGS. 1 and 5.

Figure 2:
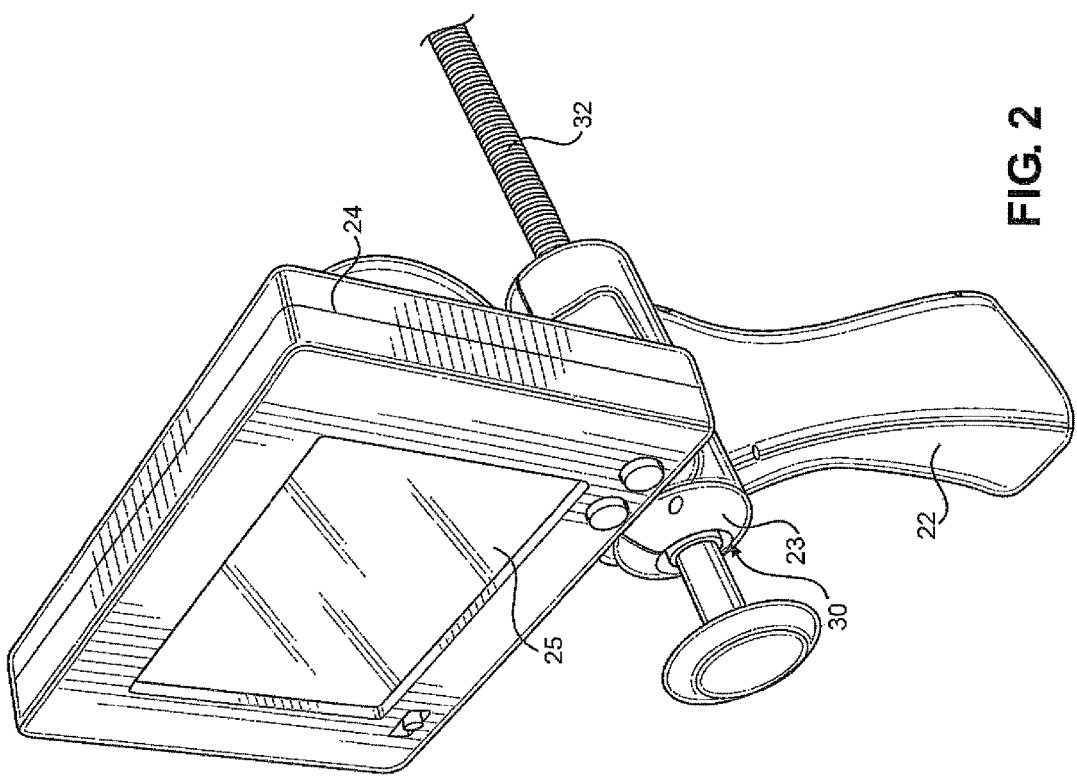
FIG. 2 is an enlarged front perspective view of the body of the invention including the handle and viewing screen.

To facilitate the grasping action of the fingers 38, a collar is secured to the control rod 34 within the open passage 30 within the body 21 of the tool. To apply a constant force on the control rod to urge the knob to the outermost position of the knob relative to the body 21, as shown in FIGS. 1 and 2, a coil spring, or other spring mechanism, is mounted about the control rod, so as to be compacted as the knob is forced toward the body of the tool. When the knob is released, the compressed spring will expand against the collar mounted about the control rod so as to draw the fingers of the grasping mechanism within the outer housing of the tool as the knob is moved to the position thereof shown in FIGS. 1 and 2.

Figure 8:
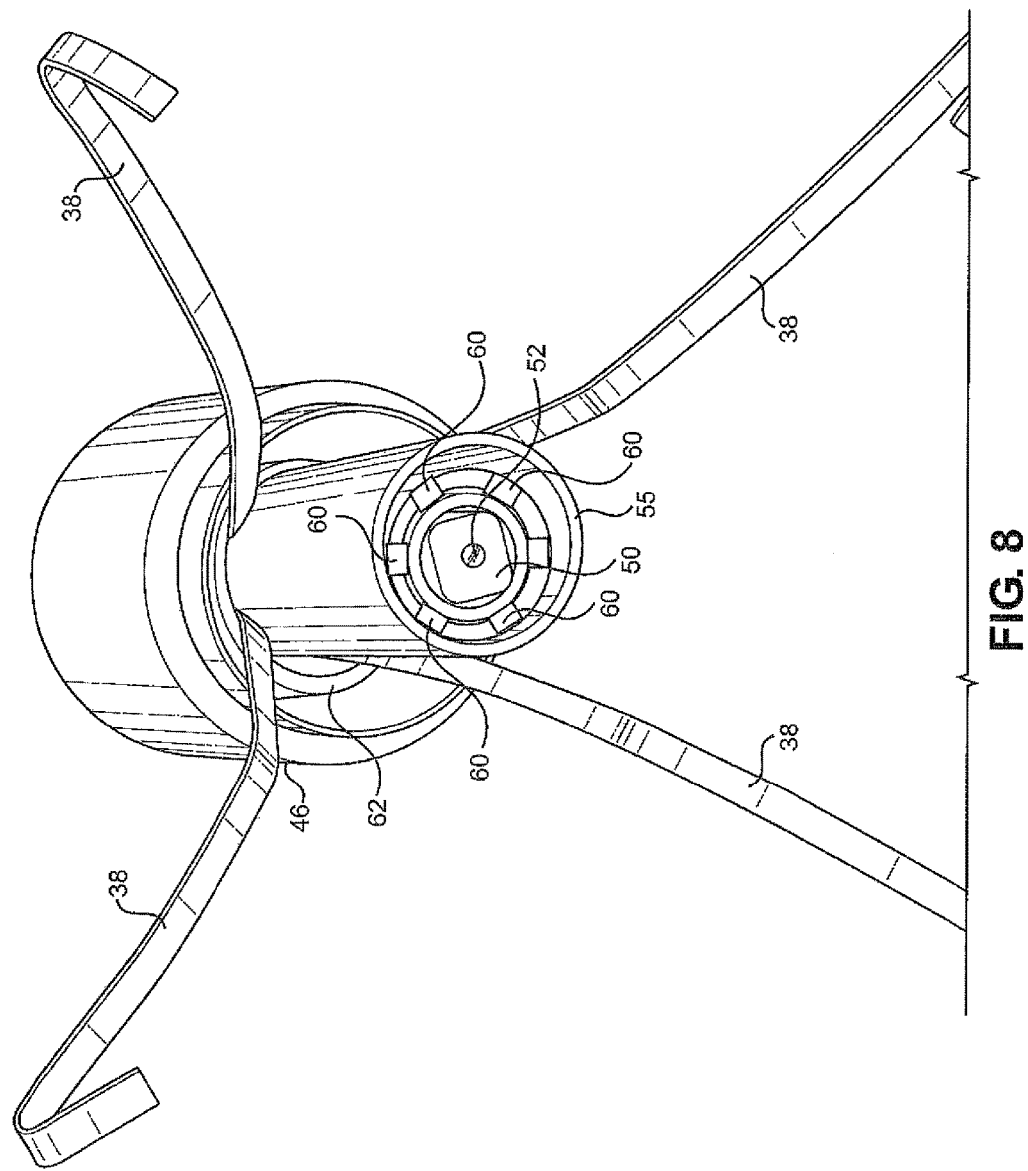
FIG. 8 is another perspective end view similar to FIG. 7 having an outer end portion of the housing removed to better show the LED's.
Figure 9:
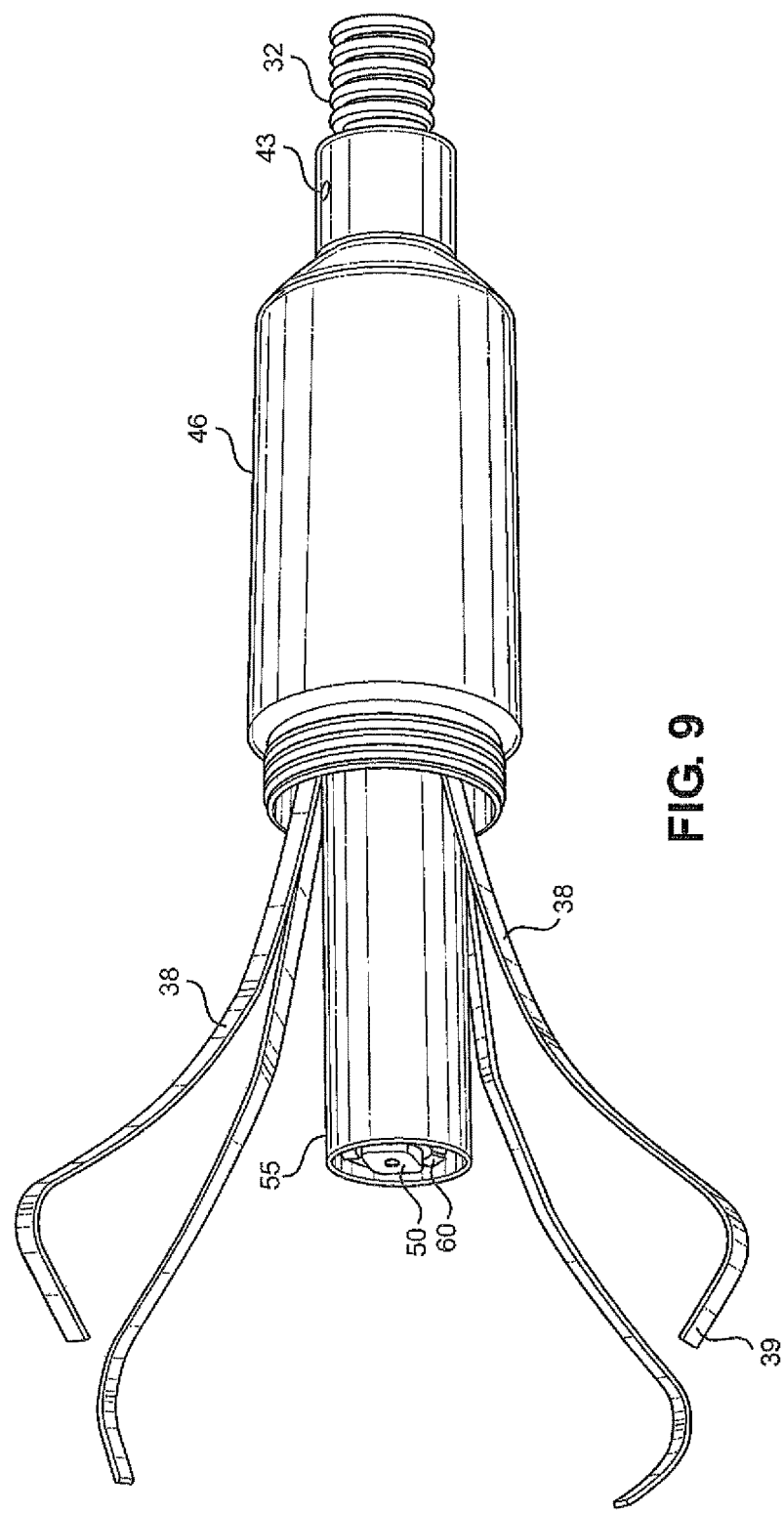
FIG. 9 is a side perspective view of the housing shown in FIG. 8.

To facilitate the use of the grasping portion of the tool to retrieve tools, parts or components located in hard to access places, the tool of the present invention incorporates a camera device 50 which is mounted in an open end portion 51 of the outermost tubular portion 44 of the two piece housing 40 as shown in FIG. 7. The camera device includes a lens 52 which is electrically connected to the viewing screen 25 by electrical wires 53, as shown in FIG. 10. To further facilitate viewing of an object to be retrieved using the tool of the present invention, a plurality of LEDs 60 are mounted within an inner tubular housing 55, see FIG. 8, disposed within the two piece housing 40. As shown in FIG. 8, six LEDs are shown mounted in surrounding relationship with respect to the camera lens 52. Fewer or additional LEDs may be used within the teachings of the present invention. Also, and as shown in FIG. 8, the grasping fingers 38 surround the inner tubular housing 55. The grasping fingers are connected to the control rod 34 within another tubular member 62 which surrounds the inner tubular housing 55, see FIGS. 8 and 10. In this manner, the outer ends of the grasping fingers will be viewable on the viewing screen when the tool is in use as is shown in FIG. 11.

With reference to FIG. 2, power to the LEDs and the camera device is controlled through an ON/OFF switch 65 mounted on the upper housing in which the viewing screen is mounted. Also mounted to the upper housing 24 are two power control buttons 66 and 68 for increasing and decreasing power from the batteries to the LEDs. The light intensity of the LEDs may be increased by depressing the button 66 and decreased by depressing button 68.

With reference to the drawings, the dimensions of one prototype of the invention are shown in millimeters, it being within the teachings of the invention to alter the sizes and dimensions of the tool and the components thereof. A viewing screen of the shown prototype may have a 3.5 inch, 89 mm, diagonal dimension. General, a maximum distance X of movement of the push knob relative to the body 21 is approximately 50 mm using a force of approximately 2 lbs. Again, a length of the control rod and the elongated flexible tubular member 32 may vary.

We claim:

1. An illuminated object viewing and retrieval tool comprising a body, including a control rod guide portion and a housing, a display screen mounted within the housing, an elongated flexible tubular member extending from the control rod guide portion of the body and a control rod extending through an open passage of the control rod guide portion to an inner end, the control rod also extending from the body through the flexible tubular member to an outer housing which is secured to an outer end portion of the flexible tubular member, a grasping mechanism mounted so as to be movable with respect to an outer open end of the outer housing from a non-deployed position within the outer housing to a deployed position where finger elements of the grasping mechanism expand outwardly relative to one another and the open end of the outer housing, the grasping mechanism further mounted as to be returned to the non-deployed position from the deployed position by expansion of a spring compressed between the control rod guide portion of the body and a knob attached to an end of the control rod opposite of the grasping mechanism, the grasping mechanism connected to the control rod to be movable relative to the outer housing, a camera device mounted within the outer housing, the camera device having a lens oriented to record images through the outer open end of the outer housing, a light source mounted within the outer housing adjacent the camera lens to cast light outwardly of the outer open end of the outer housing, and electrical circuits for connecting the camera device, the light source and display screen to a source of power and the camera device to the display screen so that images from the camera lens may be viewed on the display screen while illumination of the area being viewed by the camera lens is facilitated by light from the light source.

2. The illuminated object viewing and retrieval tool of claim 1 wherein the light source includes a light emitting diode mounted to the outer housing.

3. The illuminated object viewing and retrieval tool of claim 2 wherein the light source includes a plurality of light emitting diodes spaced about the camera lens.

4. The illuminated object viewing and retrieval tool of claim 1 wherein the body includes a handle extending from the control rod guide portion.

5. The illuminated object viewing and retrieval tool of claim 4 wherein the handle includes overmolded portions to facilitate gripping of the handle.

6. The illuminated object viewing and retrieval tool of claim 4 including a knob mounted to an inner end of the control rod.

7. The illuminated object viewing and retrieval tool of claim 6 including a battery compartment within the handle.

8. The illuminated object viewing and retrieval tool of claim 1 including a knob mounted to an inner end of the control rod.

9. The illuminated object viewing and retrieval tool of claim 8 including a battery compartment within the handle.

10. The illuminated object viewing and retrieval tool of claim 3 wherein the outer housing includes innermost and outermost portions, the innermost portion being connected to the outer end portion of the flexible tubular member and the outermost portion surrounding the plurality of light emitting diodes and the camera lens.

11. The illuminated object viewing and retrieval tool of claim 10 including an inner housing mounted within the outer housing, the plurality of light emitting diodes and the camera lens being mounted within the inner housing.

12. The illuminated object viewing and retrieval tool of claim 11 wherein the finger elements of the grasping mechanism are movable between the inner housing and the outer housing.

13. The illuminated object viewing and retrieval tool of claim 12 wherein the finger elements are resiliently deployed outwardly relative to one another when being moved from the non-deployed to the deployed position thereof.

14. The illuminated object viewing and retrieval tool of claim 1 wherein the finger elements are resiliently deployed outwardly relative to one another when being moved from the non-deployed to the deployed position thereof.

15. The illuminated object viewing and retrieval tool of claim 1 wherein the outer housing includes innermost and outermost portions, the innermost portion being connected to the outer end portion of the flexible tubular member and the outermost portion surrounding the sight source and the camera lens.

16. The illuminated object viewing and retrieval tool of claim 15 including an inner housing mounted within the outer housing, the light source and the camera lens being mounted within the inner housing.

17. The illuminated object viewing and retrieval tool of claim 16 wherein the finger elements of the grasping mechanism are movable between the inner housing and the outer housing.

18. The illuminated object viewing and retrieval tool of claim 17 wherein the finger elements are resiliently deployed outwardly relative to one another when being moved from the non-deployed to the deployed position thereof.

* * * * *